US009138194B1

(12) United States Patent
McGinley

(10) Patent No.: US 9,138,194 B1
(45) Date of Patent: Sep. 22, 2015

(54) APPARATUS FOR USE TO REPLICATE SYMPTOMS ASSOCIATED WITH VASCULAR OBSTRUCTION SECONDARY TO VASCULAR COMPRESSION

(71) Applicant: Joseph McGinley, Casper, WY (US)

(72) Inventor: Joseph McGinley, Casper, WY (US)

(73) Assignee: Joseph McGinley, Casper, WY (US)

( * ) Notice: Subject to any disclaimer, the term of this patent is extended or adjusted under 35 U.S.C. 154(b) by 25 days.

(21) Appl. No.: 13/871,878

(22) Filed: Apr. 26, 2013

Related U.S. Application Data

(60) Provisional application No. 61/664,841, filed on Jun. 27, 2012.

(51) Int. Cl.
*A61B 6/03* (2006.01)
*A61B 6/00* (2006.01)

(52) U.S. Cl.
CPC .. *A61B 6/03* (2013.01); *A61B 6/504* (2013.01)

(58) Field of Classification Search
CPC ...... A61B 5/03; A61B 5/4519; A61B 5/0053; A61B 5/4504; A61B 5/4528; A61B 5/6807; A61B 5/6829
See application file for complete search history.

(56) References Cited

U.S. PATENT DOCUMENTS

| | | | | |
|---|---|---|---|---|
| 3,629,581 | A * | 12/1971 | Smith | 378/209 |
| 3,766,384 | A * | 10/1973 | Anderson | 378/209 |
| 5,217,488 | A * | 6/1993 | Wu | 606/241 |
| 5,991,651 | A * | 11/1999 | LaBarbera | 600/415 |
| 6,000,399 | A * | 12/1999 | Choy | 128/845 |
| 6,326,020 | B1 | 12/2001 | Kohane et al. | |
| 6,577,887 | B2 * | 6/2003 | Wolff et al. | 600/411 |
| 6,708,693 | B1 * | 3/2004 | Choy et al. | 128/845 |
| 7,381,186 | B2 | 6/2008 | Ueno et al. | |
| 8,539,621 | B2 * | 9/2013 | West | 5/621 |
| 2002/0193683 | A1 * | 12/2002 | Danielsson et al. | 600/411 |
| 2005/0113663 | A1 * | 5/2005 | Tamez-Pena et al. | 600/407 |

(Continued)

FOREIGN PATENT DOCUMENTS

WO 0228425 4/2002
WO 2010082837 7/2010

OTHER PUBLICATIONS

Litwiller, Daniel V., et al. "Chronic exertional compartment syndrome of the lower extremities: improved screening using a novel dual birdcage coil and in-scanner exercise protocol." Skeletal radiology 36.11 (2007): 1067-1075.*

(Continued)

*Primary Examiner* — Unsu Jung
*Assistant Examiner* — Carolyn Pehlke
(74) *Attorney, Agent, or Firm* — Marsh Fischmann & Breyfogle LLP

(57) ABSTRACT

An apparatus for use with an imaging device for imaging a portion of a patient during exertion by the patient. The apparatus may include a first anchor for opposing a force applied by the patient to the first anchor in response to flexing one or more muscles in the imaged portion of the patient. There may also be provided second anchors that assist in restricting motion of the patient in response to the force applied to the first anchor. A plurality of fiducial markings may be provided that are evident in the obtained image to define a reference in the image for determining a location of a region of interest within the portion of the patient relative to the fiducial markings. The region of interest may correspond to an indication of a condition or disease (e.g., exertional compartment syndrome).

22 Claims, 14 Drawing Sheets

(56) References Cited

U.S. PATENT DOCUMENTS

| | | | |
|---|---|---|---|
| 2005/0165293 A1* | 7/2005 | Carter et al. | 600/407 |
| 2006/0025686 A1 | 2/2006 | Ueno et al. | |
| 2006/0257503 A1 | 11/2006 | Eversole | |
| 2007/0238949 A1* | 10/2007 | Wang et al. | 600/407 |
| 2007/0258992 A1 | 11/2007 | Atassi | |
| 2008/0031414 A1* | 2/2008 | Coppens | 378/65 |
| 2008/0200802 A1* | 8/2008 | Bhavaraju et al. | 600/426 |
| 2009/0318802 A1* | 12/2009 | Boyden et al. | 600/437 |
| 2010/0041765 A1 | 2/2010 | Campbell et al. | |
| 2012/0046540 A1* | 2/2012 | Branch et al. | 600/415 |
| 2013/0022543 A1 | 1/2013 | McGinley | |
| 2013/0204119 A1* | 8/2013 | Coelho Do Sameiro Espregue Mendes | 600/411 |

OTHER PUBLICATIONS http://chrisevans3d.com/files/reference/thigh_leg_muscles.pdf, May 17, 2008.*

Lecocq, J., C. Blaes, and M. E. Isner. "Exercise-induced compartment syndrome treated by botulinum toxin." Annals of Physical and Rehabilitation Medicine 54 (2011): e124-e125.*

Isner-Horobeti, Marie-Eve, et al. "Intramuscular Pressure Before and After Botulinum Toxin in Chronic Exertional Compartment Syndrome of the Leg A Preliminary Study." The American journal of sports medicine 41.11 (2013): 2558-2566.*

A. Tucker. "Chronic Exertional Compartment Syndrome of the Leg," Curr Rev Musculoskelet Med (2010) 3:32-37 Sep. 2, 2010.

J. Tipton. "Obturator Neuropathy," Curr Rev Musculoskelet Med (2008) 1:234-237 Jun. 11, 2008.

H. Gray. "Anatomy of The Human Body; The Arteries of the Lower Extremity." http://www.bartleby.com/107/157.html Mar. 5, 2015.

M. Frink. "Compartment Syndrome of the Lower Leg and Foot," Clin Orthop Relat Res (2010) 468:940-950 May 27, 2009.

R. Eberhardt. "Chronic Venous Insufficiency," Circulation by the American Heart Association (2005) 111:2398-2409 Jan. 1, 2005.

M. Bong, "Chronic Exertional Compartment Syndrome, Diagnosis and Managment," Bulletin—Hospital for Joint Diseases (2005), vol. 62, No. 3 & 4, p. 77-84 Jan. 1, 2005.

Medhelp, Botox for Peripheral Neuropathy; http://www.medhelp.org/posts/neurology/Botox-for-peripheral-neuropathy/show/452571 Mar. 1, 2008.

Styf, et al., "Intramuscular Pressue and Muscle Blood Flow During Exercise in Chronic Compartment Syndrome," British Editorial Society of Bone and Joint Surgery, vol. 69 B. 2, Mar. 1987, p. 301-305 Mar. 1, 1987.

Fraipont, et al., Chronic Exertional Compartment Syndrome, J Am Acad Orthop Surg 2003; 11:268-276 Aug. 1, 2003.

UWHC, "Common Regional Nerve Blocks," Quick Guide developed by UWHC Acute Pain Service, Jan. 1, 2011.

Gajraj, "Botulinum Toxin A. Injection of the Obturator Internus Muscle for Chronic Perineal Pain," The Journal of Pain, vol. 6, No. 5, May 2005, pp. 333-337 May 1, 2005.

Ferre, MD, et al., "Emergency physicians can easily obtain ultrasound images of anatomical landmarks relevant to lumbar puncture," American Journal of Emergency Medicine, 2007, 25, 291-296 Jan. 1, 2007.

Schubert, Exertional compartment Syndrome: Review of the Literature and Proposed Rehabilitation Guidelines Following Surgical Release, Int J Sports Physical Therapy. 2011; 126-141 Jan. 1, 2011.

* cited by examiner

APPARATUS FOR USE TO REPLICATE SYMPTOMS ASSOCIATED WITH VASCULAR OBSTRUCTION SECONDARY TO VASCULAR COMPRESSION

CROSS REFERENCE TO RELATED APPLICATIONS

This application claims benefit to U.S. Application No. 61/664,841 filed on Jun. 24, 2012 entitled "APPARATUS FOR USE TO REPLICATE SYMPTOMS ASSOCIATED WITH VASCULAR OBSTRUCTION SECONDARY TO VASCULAR COMPRESSION", the entirety of which is incorporated by reference herein.

BACKGROUND

A number of diseases have been identified that may involve transient vascular obstruction secondary to vascular compression resulting in symptoms such as pain in the affected area. For example, chronic exertional compartment syndrome, also known as exercise-induced compartment syndrome, is a disease that generally impacts athletes and can be debilitating. It is caused by reversible ischemia in an affected compartment (i.e., an anatomical space bounded by fascia, bone, etc.) resulting from vascular compression during exertion of muscle(s) in the compartment. Other diseases associated with transient vascular obstruction secondary to vascular compression may also be presented in patients such as, for example, popliteal artery entrapment syndrome.

In the case of exertional compartment syndrome, the patient may feel pain, for example in the calf, which increasingly worsens with exercise. Exertional compartment syndrome is severely painful and may affect high level athletes. The pain typically centers in the calf muscles and progressively worsens with higher levels of activity. The pain is sometimes described by patients as increasing pain and pressure under the skin. The symptoms can seem to the patient to get progressively worse but, in the case of advanced athletes, they may continue to train and exercise to meet goals.

It is believed that the symptoms of pain and tightness are the result of pressure that builds up within one or more muscle compartments of a patient, typically in a limb such as the leg or arm and most typically in the leg. Muscles are surrounded by tight tissue known as fascia, and in normal use the fascia has sufficient space for allowing muscles to function properly. However, in the case of athletes or other exertional use, as activity increases, so may blood flow increase to the muscle. Muscle size increases, but if the fascia is too constrictive, blood flow adjacent to the constricted muscle can be interrupted. Lack of blood flow may lead to ischemia and associated pain.

Previous methods for diagnosis of exertional compartment syndrome may be imprecise and ineffective for determining the location responsible for the interruption in blood flow, thus making treatment of the syndrome more difficult. For example, the symptoms of exertional compartment syndrome may only be present during exertion of one or more muscles in the patient, and any examination of the affected muscle(s) or compartment(s) during exertion may currently be impractical. Accordingly, previous methods for diagnosis of exertional compartment syndrome may include the patient exercising until symptoms develop. Once symptoms have developed, the exercise may be stopped and inter-compartment pressures of the affected area of the patient may be measured (e.g., by an insertable pressure transducer or the like).

However, upon termination of the exercise the potential causes of the symptoms (e.g., increased muscle size, increased blood flow, etc.) may also be terminated such that the symptoms of exertional compartment syndrome may begin to be reduced or alleviated at the termination of the exertion. Thus, upon termination of the exercise, the symptoms may become difficult to detect and/or fleeting. Furthermore, while detection of elevated pressures in compartments of the patient may be indicative of exertional compartment syndrome, increased compartment pressures alone may not be sufficient to identify the location of the interruption of blood flow that is a root cause of the elevated compartment pressures.

SUMMARY

It is recognized that medical imaging may be used to help diagnose and/or treat diseases associated with transient vascular obstruction secondary to vascular compression during exertion if a patient may continue to exert muscle(s) in the affected regions while remaining sufficiently stationary to obtain a medical image. In this regard, apparatuses and methods are described herein that may be used in conjunction with an imaging device to obtain an image of the patient during exertion to assist in the diagnosis or treatment of a disease associated with exertion by the patient. For example, the apparatuses and methods described herein may be used to diagnose a disease associated with transient vascular obstruction secondary to vascular compression and/or determine a location of the obstruction to assist in treatment.

Accordingly, a first aspect disclosed herein includes an apparatus for use with an imaging device for obtaining an image of a patient for use in determining a location of a region of interest corresponding to a disease associated with transient vascular obstruction secondary to vascular compression (e.g., exertional compartment syndrome or popliteal artery entrapment syndrome). The apparatus includes a patient support member and a first anchor member. The patient support member may supportably engage a patient and may be positionable with respect to the imaging device to dispose at least a portion of the patient in an imaging field of the imaging device. The first anchor may be provided to maintain a fixed position relative to the imaging device and support member during obtainment of an image of the portion of the patient. The first anchor may be contactable by the patient when the patient is supported by the patient support member. The first anchor is also operable to oppose a force applied by the patient in response to a flexing of a muscle of the patient within the portion of the patient disposed in the imaging field. In this regard, the patient may remain substantially stationary with respect to the imaging device even during exertion. Accordingly, the muscle may be flexed during the obtainment of the image. The apparatus also includes a plurality of fiducial markings that are located within the imaging field and apparent in the image. The fiducial markings provide a reference in the image for determining the location of the region of interest within the portion of the patient relative to the fiducial markings. In this regard, use of the apparatus to image the flexed muscle(s) used to exert the force against the first anchor member may allow for precise and accurate determination of the location of the source of a disease or condition in an image. In turn, the actual location of the source of the disease may be located on the patient by correlating the fiducial markings appearing in the image to those disposed adjacent to the patient.

Various feature refinements and additional features exist in relation to the first aspect. These feature refinements and additional features may exist individually or in any combination. For instance, various features discussed below in relation to any of the exemplary embodiments of the present invention may be incorporated into the first aspect alone or in any combination.

For example, the plurality of fiducial markings may be disposed on the patient support member so that when a patient is supportably engaged by the patient support member the fiducial markings extend along a selected limb of the patient. For instance, the plurality of fiducial markings may extend along the length of the limb. In another embodiment, the plurality of fiduciary markings may provide a reference to a known or determined reference point. For example, the reference point may comprise at least one of an anatomical feature of the patient or a location on the apparatus. The plurality of fiduciary markings may comprise substantially radio opaque indicia (e.g., in the case of an x-ray imaging device). Other embodiments may include fiducial markings that may be visible in an obtained image when used with other imaging techniques such fiducial markings evident in MRI images, fiducial markings evident in ultrasound imaging, etc.

In another embodiment, the apparatus may also include a second anchor spaced apart from the first anchor that may be contactable by the patient when supported by the patient support member. The second anchor may be provided to maintain a fixed position relative to imaging device and the support member during the imaging of the portion of the patient disposed in the imaging field. The second anchor may be operable to oppose the force exerted by the patient on the first anchor in response to the flexing of the muscle to maintain the portion of the patient disposed in the imaging field stationary when the muscle is flexed. The first anchor and the second anchor may be selectively positionable with respect to one another. For example, the relative position of the first anchor and the second anchor may be adjusted to accommodate patients of different sizes. Additionally, the plurality of fiducial markings may be disposed relative to at least one of the first or second anchors. In one embodiment, the second anchor may comprise a structure extending from the patient support structure that is graspably engageable by the patient.

In yet another embodiment, the first anchor may be selectively adjustable to accommodate contact by the patient when in a plurality of positions. As such, different muscles in the portion of the patient may be flexed to exert the force on the first anchor corresponding to the different respective positions of the first anchor with respect to the portion of the patient.

A second aspect includes a method for use of an apparatus for obtaining an image of a patient for determining a region of interest associated with transient vascular obstruction secondary to vascular compression. The method includes supporting a patient with respect to an imaging device, wherein at least a portion of the patient and a plurality of fiducial markings disposed relative to the portion of the patient are positionable in the imaging field of the imaging device. The method also includes obtaining an image of the portion of the patient while the patient exerts a force on a first anchor by flexing a muscle within the portion of the patient. The force may be opposed by the first anchor. The first anchor may be provided to maintain a fixed position relative to the support member and the imaging device during the imaging of the portion of the patient. The plurality of fiducial markings are apparent in the image and provide a reference in the image between the fiducial markings and the region of interest. The method also includes determining the location of the region of interest in the portion of the patient relative to the fiducial markings based on the image. Accordingly, the method may be used to precisely and accurately determine the location of a source of a disease or condition associated with transient vascular obstruction secondary to vascular compression, such as exertional compartment syndrome. That is, the region of interest associated with the disease or condition may be evident in the image obtained of the flexed muscles. This region of interest may be correlated to a location on the patient by correlation between the fiducial markings apparent in the image and those provided adjacent to the patient.

Various feature refinements and additional features exist in relation to the second aspect. These feature refinements and additional features may exist individually or in any combination. For instance, various features discussed below in relation to any of the exemplary embodiments of the present invention may be incorporated into the second aspect alone or in any combination.

For example, the region of interest may be evident in the imaging only during the exertion of the force using the muscle or muscles within the portion of the patient. The region of interest may correspond to an obstruction of blood flow in the vasculature adjacent the muscle(s) flexed to exert the force.

In another embodiment, the method may include diagnosing the patient based on the image. In yet another embodiment, the method may include treating the patient at the region of interest.

In still another embodiment, the method may include adjusting a second anchor relative to the first anchor, wherein the patient contacts the second anchor during the exertion of the force and the second member opposes the force and resists movement of the patient during the application of force.

A third aspect includes an apparatus for use with an imaging device for obtaining an image of a patient for use in determining a location of a region of interest corresponding to a disease associated with transient vascular obstruction secondary to vascular compression. The apparatus may include a patient support member and a first anchor. The patient support member may supportably engage a patient and may be positionable with respect to the imaging device to dispose at least a portion of the patient in an imaging field of the imaging device. The first anchor may be contactable by the patient when the patient is supported by the patient support member and operable to oppose a force applied by the patient in response to a flexing of a muscle of the patient within the portion of the patient disposed in the imaging field. The muscle is flexed during the obtainment of the image. Furthermore, the first anchor may be selectively adjustable between a plurality of different positions such that various different muscles in the portion of the patient may be flexed to exert the force on the first anchor based on the position of the first anchor relative to the portion of the patient.

Various feature refinements and additional features exist in relation to the third aspect. These feature refinements and additional features may exist individually or in any combination. For instance, various features discussed below in relation to any of the exemplary embodiments of the present invention may be incorporated into the third aspect alone or in any combination.

For instance, the first anchor may comprise a foot pedal, and the muscle used to exert the force on the first anchor corresponds to a muscle in the leg of the patient. The foot pedal may be adjustable in the dorsum and plantar directions with respect to the foot of the patient. The foot pedal may be adjustable in the lateral direction with respect to the foot of the patient.

The various features discussed above in relation to each aforementioned aspect may be utilized by any of the aforementioned aspects. Additional aspects and corresponding

DETAILED DESCRIPTION

Reference will now be made to the accompanying drawings, which at least will assist in illustrating the various pertinent features of the present invention. In this regard, the following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to enable others skilled in the art to utilize the invention as described or in other embodiments and with various modifications required by the particular applications or uses of the present invention.

Figure 1:
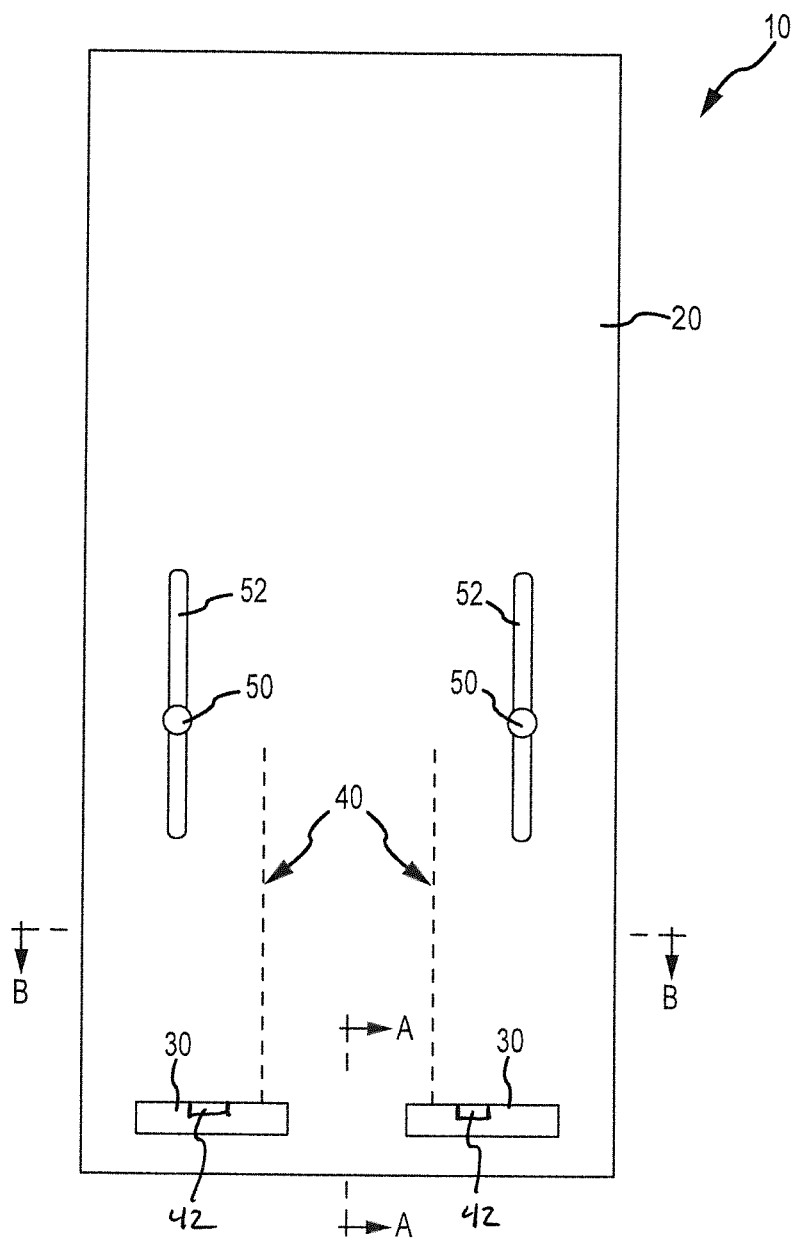
FIG. 1 is a top view of an embodiment of an apparatus.
Figure 2:
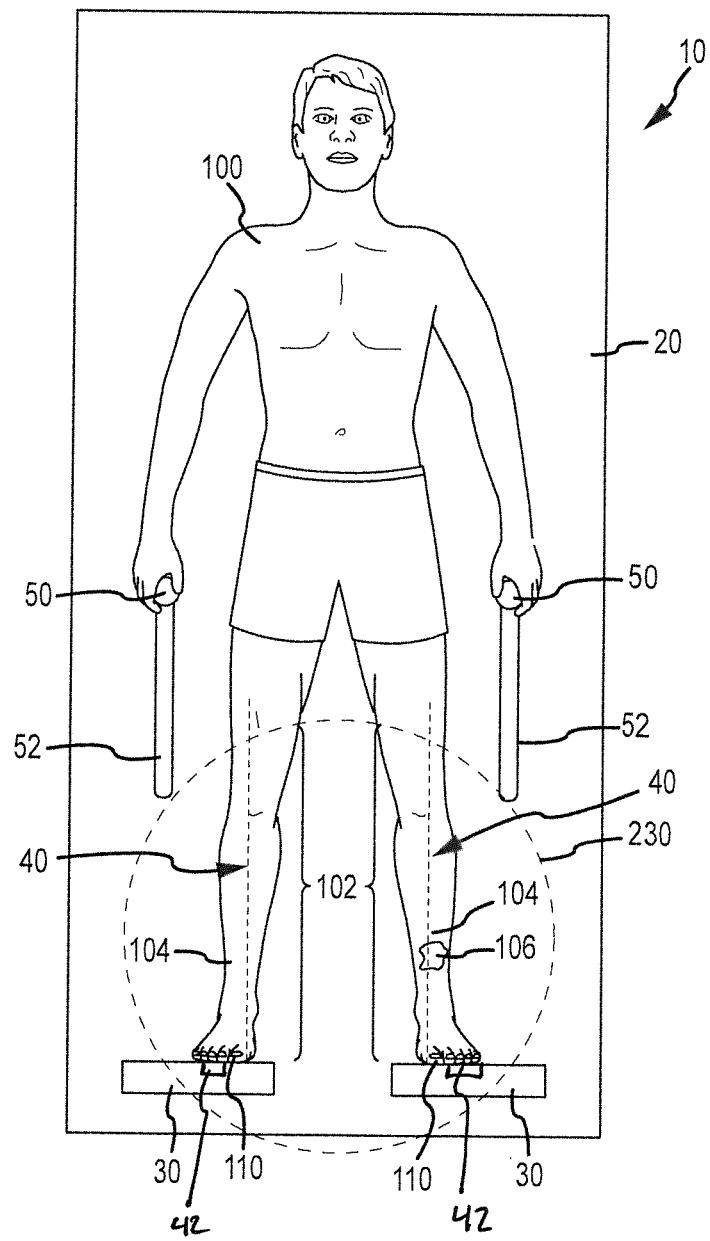
FIG. 2 is a top view of the embodiment of the apparatus of FIG. 1 with a patient supportably engaged by the apparatus.
Figure 3:
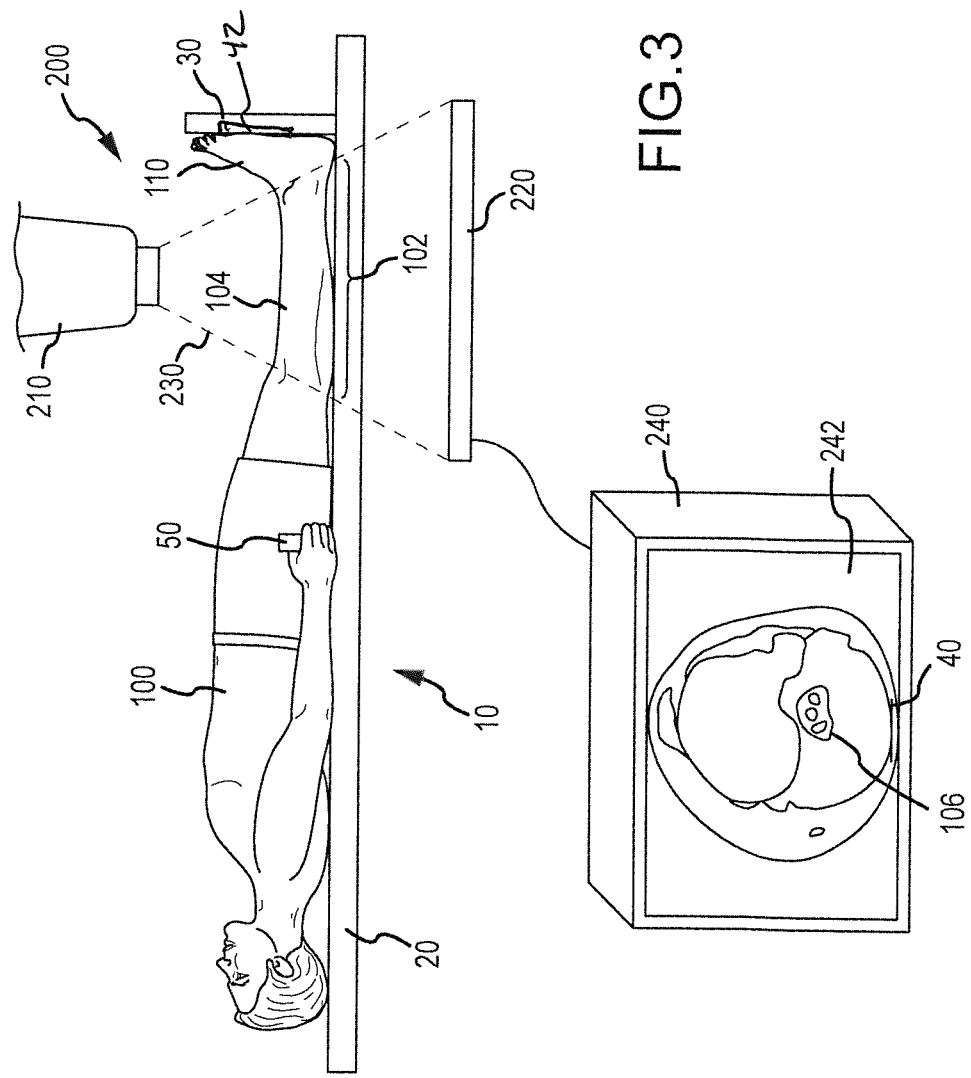
FIG. 3 is a side view of the embodiment of the apparatus of FIG. 1 disposed relative to an imaging device.

With reference to FIGS. 1-3, an embodiment of an apparatus 10 is shown. The apparatus 10 may be used in conjunction with an imaging device 200 (shown in FIG. 3) to obtain an image of a patient 100 (shown in FIGS. 2 and 3) while the patient 100 exerts a force that is opposed by a first anchor 30. Accordingly, the imaging device 200 may be used in conjunction with the apparatus 10 to diagnose and/or treat diseases associated with transient vascular obstruction secondary to vascular compression resulting from the exertion of the patient. For example, the apparatus 10 may be used to replicate the symptoms of, for example, exertional compartment syndrome and/or popliteal artery entrapment syndrome by having the patient 100 exert a force against the first anchor 30 while an image is obtained of the muscles used to exert the force.

The apparatus 10 may generally include a patient support member 20 that may support the patient 100. The support member 20 may also assist in maintaining the patient 100 stationary during the obtainment of an image while the patient 100 exerts a force that is opposed by the first member 30 using a muscle with the portion 102 of the patient 100 that is imaged. A plurality of fiducial markings 40 may be provided on the support member 20 as will be described in greater detail below. In this regard, a region of interest 106 may be identified in the patient 100 that may, for example, correspond to vascular compression or vascular obstruction.

The apparatus 10 may, for example, be particularly useful in diagnosing diseases or conditions where the etiologies of the disease are associated with exertion by the patient 100. For example, as described above, exertional compartment syndrome may occur as a result of an increase in pressure in the musculature of the patient 100 used during exertion. The increase in pressure may result from an increase in muscle size and/or increased blood flow corresponding to exertion by the patient 100. The increase in muscle size combined with the increase in blood flow may result in the blood flow of the patient 100 being interrupted such that blood flow in a portion of the vasculature (e.g., the veins of the patient 100) may be reduced or completely blocked. In turn, blood may continue to flow to the region (e.g., arterial flow), resulting in a further increase in pressure in the musculature and the worsening of symptoms.

The increase in pressure in the musculature of the patient that corresponds to exertional compartment syndrome may be evident only when the patient 100 exerts the muscle(s) adjacent to the affected vasculature. As described above, traditional means of diagnosing exertional compartment syndrome may involve having a patient exercise (e.g., on a treadmill or the like) until symptoms develop, terminating the exercise, and subsequently measuring pressure in the affected area (e.g., with an insertable pressure transducer introduced into the musculature of the patient). However, this method of diagnosis may only confirm increased pressure in the musculature of the patient and may not be able to locate the muscle(s) or locations within the muscle(s) responsible for the interrupted blood flow in the vasculature of the patient.

For instance, it may be that upon termination of the exercise, the muscle(s) responsible for the interruption of blood flow in the vasculature rest and allow blood flow to resume such that post-exercise inspection of the affected region may not be indicative of symptoms associated with the vascular obstruction. Furthermore, even if a residual increase in pressure may be detected directly after termination of exercise, the affected region of interest may not be identified. Similarly, other diseases associated with transient vascular obstruction secondary to vascular compression may also be difficult to diagnose in that the vascular compression may be present (i.e., presenting symptoms) only when the patient undergoes exertion.

Accordingly, the apparatus 10 described herein may allow for the patient 100 to continue to exert the muscle(s) responsible for the interruption of blood flow in the vasculature of the patient 100 while an image of the portion 102 of the patient 100 undergoing exertion is obtained. Thus, the region of interest 106 may be associated with a location of the interruption of blood flow in the vasculature of the patient 100 as identified in an image obtained of the portion 102 of the patient 100 undergoing exertion so that further treatment may be performed at the region of interest 106 of the patient 100.

As shown in FIG. 2, the patient 100 may rest upon a support member 20 and contact the first anchor 30. In the embodiment depicted, a plurality of first anchors 30 are shown that are contacted by respective ones of the feet 110 of the patient 100. However, it will be understood that a single first anchor 30 may be provided for opposing a force applied by the patient 100. The support member 20 may comprise a table on which the patient 100 may lie. In this regard, the support member 20 may be positionable with respect to an existing patient table of an imaging device or may be integrated with an imaging device.

The first anchor 30 may be disposed to maintain a fixed position relative to the support member 20 and the imaging device 200 during the obtainment of the image. In this regard, the first anchor 30 may be attached to the support member 20. The first anchor 30 may also be selectively positionable relative to the support member 20 as will be described in greater detail below. In any regard, the first anchor 30 may be selectively rigidly attached to the support member 20 such that the first anchor 30 remains stationary even when a force is applied thereto. As such, at least a portion of the first anchor 30 may be integrally provided with the support member 20. In another embodiment, the first anchor 30 may be affixed to the support member 20 by appropriate mechanisms such as, for example, fasteners, welding, adhesives, interlocking features, or the like.

It may be common for exertional compartment syndrome to develop within the legs 104 of a patient 100. For example, one or more of the adductor longus muscle, the sartorius muscle, the vastus intermedialis muscle, the adductor magnus muscle, the popliteus muscle, the gastrocnemius muscle, the soleus muscle, and/or the plantaris muscle may impinge on adjacent vasculature to produce the symptoms of exertional compartment syndrome. Accordingly, in one embodiment, the first anchor 30 may comprise a foot pedal that is contactable by the foot 110 of the patient 100. The patient 100 may exert the muscles within the legs 104 to apply a force upon the first anchor 30. The exertion may correspond with attempted movement of the patient's foot 110 in a plantar direction relative to the foot 110 forcing the distal aspect of the planar surface at a region of the metatarsophalangeal joint of the patient's foot 110 (i.e., the "ball" of the patient's foot 110) against the first anchor 30. Upon exertion of a force against the first anchor 30, one or more of the adductor longus muscle, the sartorius muscle, the vastus intermedialis muscle, the adductor magnus muscle, the popliteus muscle, the gastrocnemius muscle, the soleus muscle, and/or the plantaris muscle may be exerted to produce the symptoms of exertional compartment syndrome.

While contact of the ball of the foot 110 against the first anchor 30 to flex one or more of the one or more of the adductor longus muscle, the sartorius muscle, the vastus intermedialis muscle, the adductor magnus muscle, the popliteus muscle, the gastrocnemius muscle, the soleus muscle, and/or the plantaris muscle is shown and described herein, it will be understood that other muscles within the patient may also be associated with exertional compartment syndrome. Accordingly, other anchor arrangements may be provided to diagnose exertional compartment syndrome in other muscles within the leg or in different portions of the patient 100. For example, a first anchor may be provided against which the patient may exert a force with an arm, another portion of the leg 104 other than the foot 110, the abdomen, etc. One such example of an alternative first anchor arrangement 30', is discussed in greater detail below with respect to FIGS. 7 and 8.

With further reference to FIG. 3, the apparatus 10 and patient 100 may be positionable relative to an imaging device 200. The imaging device 200 may include an energy source 210 and a detector 220. The imaging device 200 may also include a display 240 in operative communication with the imaging device 200 (e.g., the detector 220) for displaying an image 242 obtained by the imaging device 200. The display 240 may be viewed by a physician or other healthcare professional to diagnose and/or treat the region of interest 106 associated with the vascular obstruction. The area between the energy source 210 and the detector 220 may be referred to as the imaging field 230. Accordingly, the apparatus 10 may be positionable with respect to the imaging device 200 such that at least a portion 102 of the patient 100 is disposed in the imaging field 230. For example, the portion 102 of the patient 100 including the muscle(s) used to exert the force against the first anchor 30 may be disposed in the imaging field 230. As shown in FIG. 3, the region of interest 106 may be identified in the image 242. The region of interest 106 may be located relative to the fiducial markings 40 appearing in the image 242 so that the location of the region of interest 106 relative to the fiducial markings 40 may be obtained.

The imaging device 200 may be any imaging device known in the art. For example, the imaging device 200 may be a computer tomography (CT) device, a magnetic resonant imaging (MRI) device, an ultra sound device, or any other appropriate medical imaging device. In one embodiment, the imaging device 200 may be a CT device used in conjunction with contrast media injected into the vasculature of the patient 100. Thus, any interruption in blood flow in the vasculature of the patient 100 may be visible in the resulting image obtained by the CT device corresponding to the region of interest 106.

As described above, a plurality of fiducial markings 40 may be provided on the patient support member 20. The fiducial markings 40, may be visible in the image 242 obtained of the portion 102 of the patient 100 in the imaging field 230 as shown in FIG. 3. In this regard, the fiducial markings 40 may be substantially radio opaque markers through which energy from the energy source 210 may not pass such that the fiducial markings 40 are evident in the obtained image 242.

The fiducial markings 40 may be aligned with respect to a limb of the patient 100 (e.g., the leg 104) along the portion 102 of the patient 100 disposed in the imaging field 230. The fiducial markings 40 may be evident in the resulting image 242 and provide a reference with respect to a region of interest 106 in the resulting image 242. For example, the fiducial markings 40 may be indicative of a distance to a region of interest 106 in the obtained image 242 from a reference. The reference may be known or determined. For example, the reference may be an anatomical feature of the patient 100 or a location on the apparatus 10 (e.g., the interface of the patient 100 and the first anchor 30). This may be beneficial because, especially in the case of an image of the patient's leg as there may be a relative lack of anatomical features near the region of interest 106 that may be used to define a position of the region of interest in the leg. Thus, adjacent fiducial markings 40 may facilitate convenient location of the region of interest 106 even in the absence of locatable adjacent anatomical features.

While shown in FIG. 1 as extending along only a portion of the apparatus 10, it will be understood that the fiducial markings 40 may extend along an entirety of the apparatus 10 or additional fiducial markings 40 may be provided in one or more other locations on the apparatus 10 (e.g., adjacent to and/or extending along the abdomen, arms, or head of the patient 100). In any regard, the fiducial markings 40 that are visible in the image 242 obtained of the portion 102 of the patient 100 may be used to reference a region of interest 106 so that the region of interest 106 may be located on the patient 100 relative to the fiducial markings 40 as will be described in greater detail below.

The first anchor 30 may oppose a force applied thereto by the patient 100 as a result of the flexing of one or more muscles in the portion 102 of the patient 100 disposed in the imaging field 230. Accordingly, any interruption of blood flow in the vasculature of the patient 100 adjacent to the flexed muscle(s) may be apparent in an image obtained while the patient 100 is flexing the muscle(s).

While the first anchor 30 may be operable to oppose the force applied by the patient 100, it will be appreciated that upon application of a force by the patient 100 on the first anchor 30, the patient 100 may have a tendency to undergo movement relative to the first anchor 30 as a result of the application of a force thereto. Accordingly, the first anchor 30 may be operable to oppose the force applied thereto by the patient 100 while maintaining the patient 100 substantially stationary for the purpose of obtaining an image of the portion 102 of the patient 100. For example, the first anchor 30 may be resistibly deflectable upon application of a force thereto such that the portion 102 of the patient 100 remains stationary during the exertion of a force against the first anchor 30. That is, the first anchor 30 may be biased against the application of the force by the patient 100. For example, the first anchor 30 may be spring loaded or include an elastically deformable portion to resist the force while allowing deflection so as to maintain the patient 100 substantially stationary during the application of the force.

However, the symptoms associated with exertional compartment syndrome may be produced when the patient is at or near maximal exertion of the muscle(s). Therefore, it may be that the force applied by the patient against the first anchor 30 needed to produce the symptoms of exertional compartment syndrome may exceed the force of static friction acting between the patient 100 and the support member 20 such that the patient 100 may move away from the first anchor 30 in response to the application of a force great enough to result in the symptoms of exertional compartment syndrome. In this regard, the apparatus 10 may include second anchors 50 to further oppose movement of the patient 100 when applying the force to the first anchors 30. In this regard, the second anchors 50 may be provided to maintain a fixed position relative to the imaging device 200 and the support member 20 during the imaging. The second anchors 50 may be contactable by the patient 100 to oppose any movement resulting in the application of force to the first anchor 30. For example, the second anchors 50 may comprise hand grips extending from the support member 20 that are graspable by the patient 100. In other embodiments, the second anchors may comprise other arrangements operable to resist a sliding movement of the patient 100 on the support member 20. For example, shoulder restraints, straps secured over, or gasped by, the patient 100, or other means of restricting movement of the patient 100 away from the first anchors 30 may be provided.

The second anchors 50 may be adjustable with respect to the first anchor 30. For example, the second anchors 50 may be positionable along a slot 52 provided in the support member 20. The second anchors 50 may be selectively positioned along the slot 52 to, for example accommodate patients 100 of different sizes. The second anchors 50 may be secured with respect to the support member 20 along the slots 52 by any known mean in the art. For example, a fastener may be provided with each of the second anchors 50 and selectively tightened to secure the anchors 50 along the slot 52. As such, the second anchors 50 may be infinitely adjustable along the length of the slots 52. In another embodiment, a plurality of discrete positions may be provided for the second anchors 50 (e.g., a plurality of through holes in the support member may be defined). In another embodiment, a plurality of predetermined locations may be provided along the slots 52 (e.g., defined by detents, holes, or other means of securing the second anchors 50 to the support member 20). As such, the second anchors 50 may be selectively positionable at one of the predetermined locations on the support member 20.

The first anchor 30 may be adjustable to accommodate a plurality of different positions of the patient 100 while applying a force thereto. For example, the first anchor 30 may be adjustable such that the foot 110 of the patient 100 may contact the first anchor 30 at different angles relative to the leg 104 of the patient 100 depending on the position of the first anchor 30. Furthermore, the first anchor 30 may be adjustable in a number of different respects. In this regard, a plurality of different positions of the first anchor 30 may be established. It may be that the different positions of the first anchor 30 result in a different muscle or muscles in the leg 104 of the patient 100 being used to exert a force against the first anchor 30. Thus, the first anchor 30 may be adjusted so as to target the use of a particular muscle or muscles that are suspected to be responsible for the symptoms of the condition to be diagnosed or treated.

Figure 4:
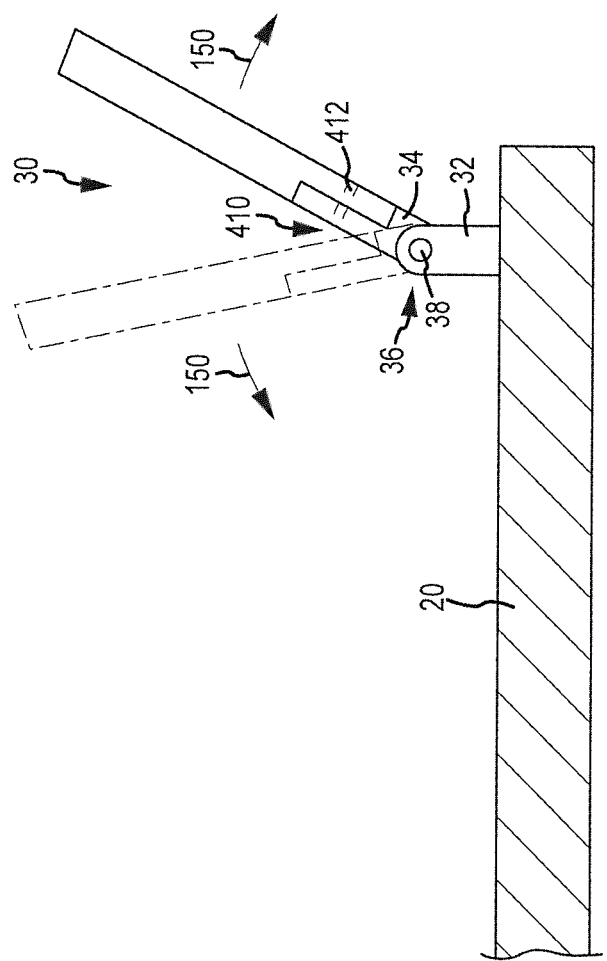
FIG. 4 is a cross sectional view taken along section line A-A in FIG. 1.
Figure 5:
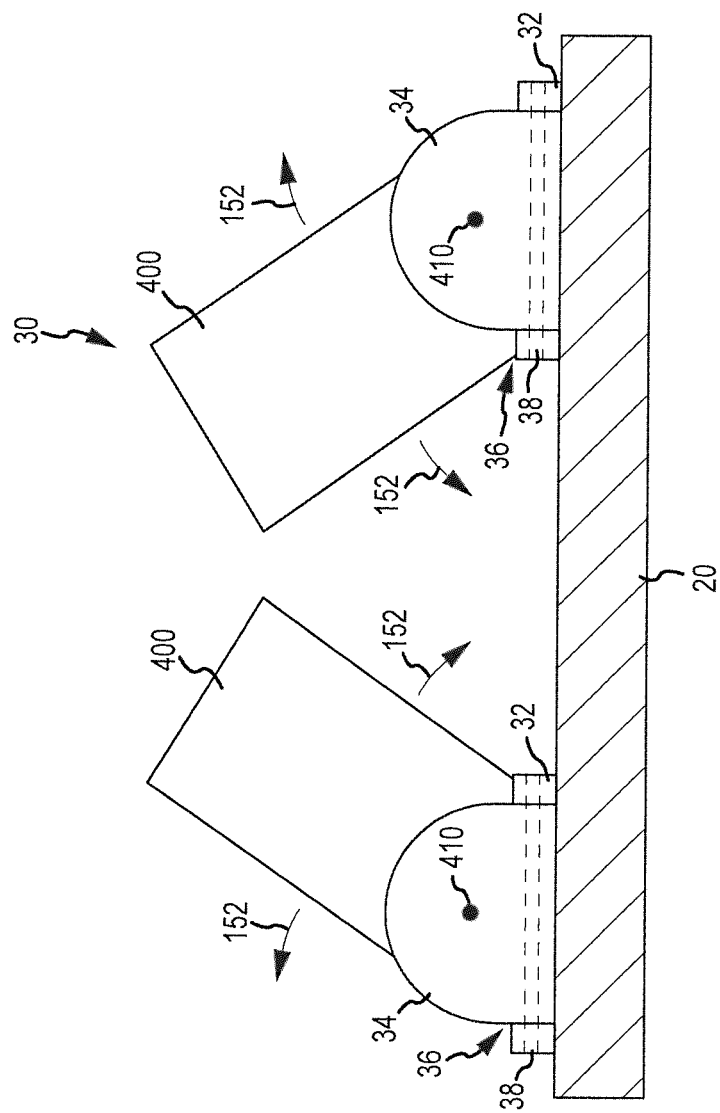
FIG. 5 is a cross sectional view taken along section line B-B in FIG. 1.

In this regard, with further reference to FIG. 4, the first anchor 30 may be adjustable in a direction corresponding to deflection of the foot 110 of the patient 100 in the dorsum and plantar directions. In this regard, the first anchor 30 may include a base portion 32 and a positionable portion 34 secured to the base portion 32 at a joint. For instance, as shown in FIGS. 4 and 5, the base portion 32 may be secured to the positionable portion 34 by way of a hinge 36. In this regard, the positionable portion 34 may be pivotal with respect to the base member 32 about the hinge 36. For example, the hinge 36 may comprise an axle 38 extending through the base portion 32 and the positionable portion 34 that allows for pivotal movement of the positionable portion 34 relative to the base portion 32.

The positionable portion 34 may be secured relative to the base portion 32 in a plurality of different positions. In this regard, a fastener may be provided (e.g., relative to the axle 38) to restrain movement between the positionable portion 34 and the base portion 32. In this regard, the positionable portion 34 may be secured with respect to the base portion 32 and selectively moveable between a plurality of different positions in the dorsum/plantar direction (indicated in FIG. 4 by arrows 150). For example, one other position of the first anchor 30 in the dorsum/plantar direction is shown in phantom in FIG. 4.

Furthermore, the first anchor 30 may be positionable in the lateral and medial direction (corresponding to arrows 152 in FIG. 5) with respect to the leg 104 of the patient 100. In this regard, the positionable portion 34 may include a laterally adjustable portion 400 moveable relative to the positionable portion 34. In this regard, the laterally adjustable portion 400 may be selectively positionable relative to the positionable portion 34 in a plurality of different positions in the lateral/medial direction 152. For example, the laterally adjustable portion 400 may be pivotal relative to the position portion 34 about a pivot 410. In this regard, a fastener 412 may pass through the laterally adjustable portion 400 and/or the positionable portion 34 at the pivot 410. Upon loosening of the fastener 412, the laterally adjustable portion 400 may be moved relative to the positionable portion 34. Once the fastener is tightened, the laterally adjustable portion 400 may be secured relative to the positionable portion 34.

The first anchors 30 shown may be infinitely adjustable in both the lateral/medial direction 152 (e.g., corresponding to movement between the laterally adjustable portion relative to the positionable portion) and the dorsal/plantar direction 150 (e.g., corresponding to movement between the positionable portion relative to the base portion). In another embodiment, a plurality of discrete positions in either or both of the lateral/medial (direction 152) and dorsal/plantar direction 150 may be established. In this regard, as discussed briefly above, the first anchor 30 may be adjusted so as to target the use of a particular muscle or muscles that are suspected to be causing the symptoms of the condition to be diagnosed or treated. That is, when the first anchor 30 is disposed in different relative configurations by selective positioning of the positionable portion 34 and/or the laterally adjustable portion 400, different muscles of the patient 100 may be exerted to apply a force to the first anchor 30.

Furthermore, the first anchor 30 may include one or more measurement instruments 42 that may be operable to determine the amount of force and/or pressure being applied to the first anchor 30 by the patient. In various embodiments, the measuring instrument 42 may be located at or integrated with the first anchor 30. In one embodiment, the measuring instrument 42 may include a strain gauge for determining a force value applied to the first anchor 30. Furthermore, a force and/or pressure value determined by the measurement instrument 42 may be recorded or displayed (e.g., on display 240) such that the value is perceivable by a user. In this regard, the amount of force and/or pressure being applied by the patient to the first anchor 30 may be monitored.

Figure 6:
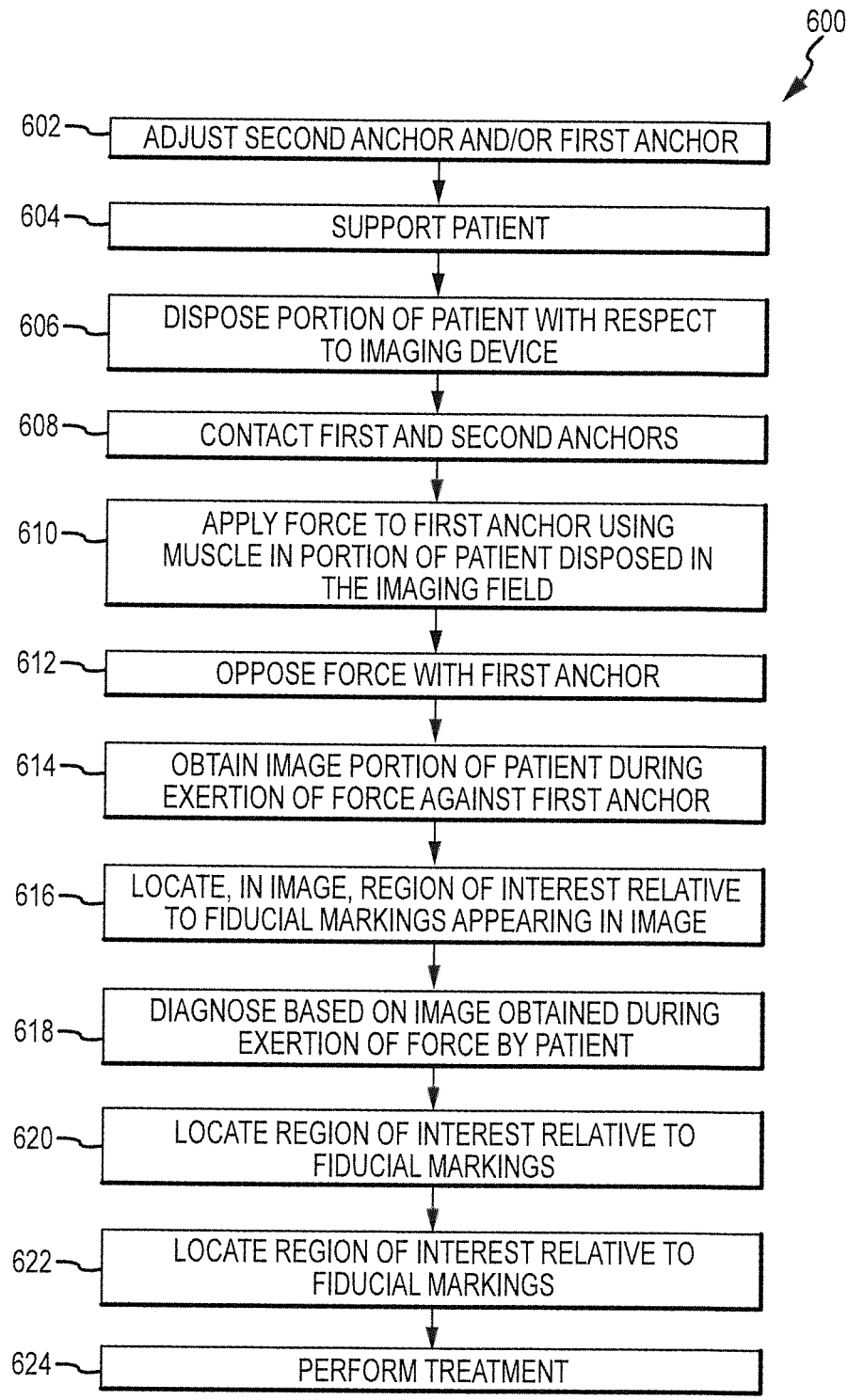
FIG. 6 is a flow chart depicting an embodiment of a method of use of an apparatus for imaging a patient during exertion by the patient.

FIG. 6 illustrates an embodiment of a method 600 that may be performed in conjunction with, for example, an apparatus 10 described above for the imaging of a portion of a patient 100 during exertion by the patient 100. The method 600 may include adjusting 602 the first anchor 30 and/or the second anchor 50. In this regard, the adjusting 602 may include positioning the positionable portion 34 and/or the laterally adjustable portion 400 of the first anchor 30 in a predetermined position. The predetermined position may be chosen based on a targeted muscle or muscles to be flexed during application of force by the patient 100 to the first anchor 30.

Furthermore, the second anchors 50 may be adjusted 602 relative to the first anchor 30. The adjusting 602 may be to accommodate patients 100 of different sizes. Accordingly, the adjusting 602 may be performed once the patient 100 is supported by the support member 20 or a measurement may be taken from the patient 100 and used to adjust the second anchor 50.

The method 600 may also include supporting 604 the patient 100. In one embodiment, the patient 100 may lie on the support member 200. The method 600 may also include disposing 606 a portion 102 of the patient 100 relative to an imaging device 200. For example, the portion 102 of the patient 100 including the muscles to be flexed to produce the force against the first anchor 30 may be disposed 606 in the imaging field 230 of the imaging device 200.

The method 600 may also include contacting 608 the first anchor 30 and the second anchor 50. In this regard, the method 600 may also include applying 610 a force to the first anchor 30 utilizing a muscle or muscles in the portion 102 of the patient 100 disposed in the imaging field 230 of the imaging device 200. The method 600 may include opposing 612 the force with the first anchor 30. The amount of force applied by the patient 100 may be monitored (e.g., via measurement instrument 42). In this regard, the amount of force applied by the patient 100 may be selectively varied and confirmed by way of the monitoring or the force may be maintained at a constant level by way of monitoring.

The method 600 may further include obtaining 614 an image 242 of the portion 102 of the patient 100 during the application 610 of the force by the patient 100 against the first anchor 30. In turn, the method 600 may include locating 616 a region of interest 106 in the resulting image 242. The locating 616 may include determining the relative location of the region of interest 106 relative to fiducial markings 40 appearing in the image 242. The method 600 may further include diagnosing 618 a disease based on the image 242 obtained 614 during the application 610 of the force by the patient 100. For instance, the diagnosis or treatment may generally be provided as described in U.S. Pat. Pub. No. 2013/0022543, the entirety of which is incorporated by reference herein.

The method 600 may further include locating 620 on the patient 200 the region of interest 106 relative to the fiducial markings 40 on the support member 20. In this regard, the actual location of the region of interest 106 may be located 620 on the patient 100. In turn, the method 600 may include performing 624 treatment at the region of interest 106 on the patient 100 to alleviate the symptoms and/or cause of the disease.

Figure 7:
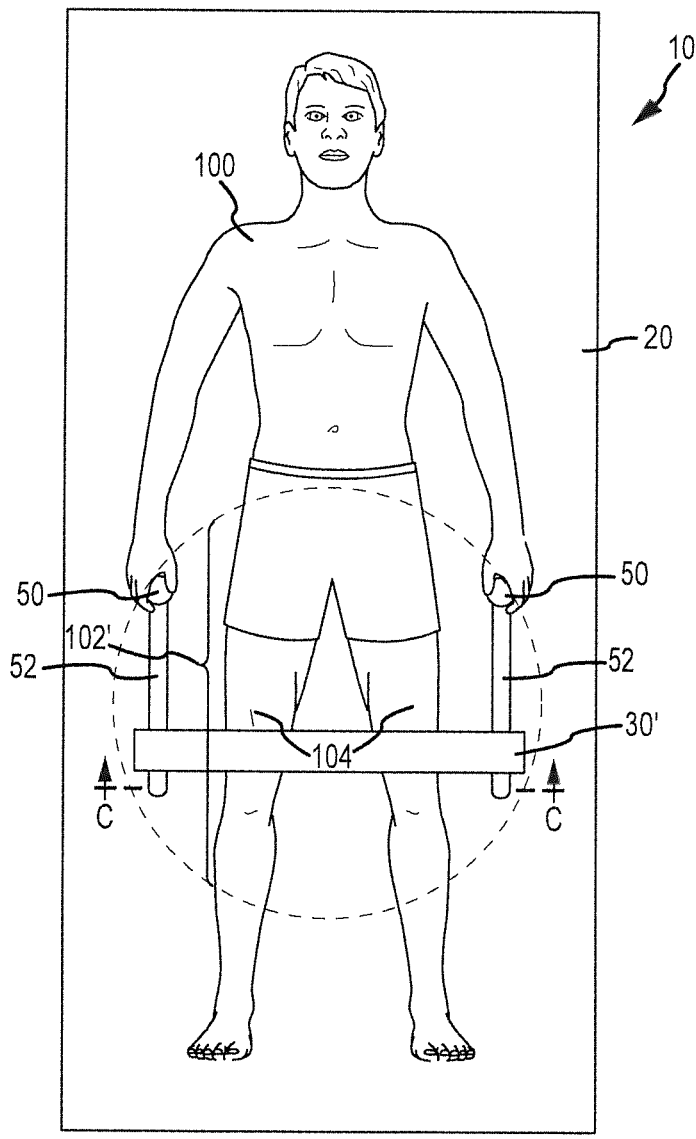
FIG. 7 is another embodiment of an apparatus.
Figure 8:
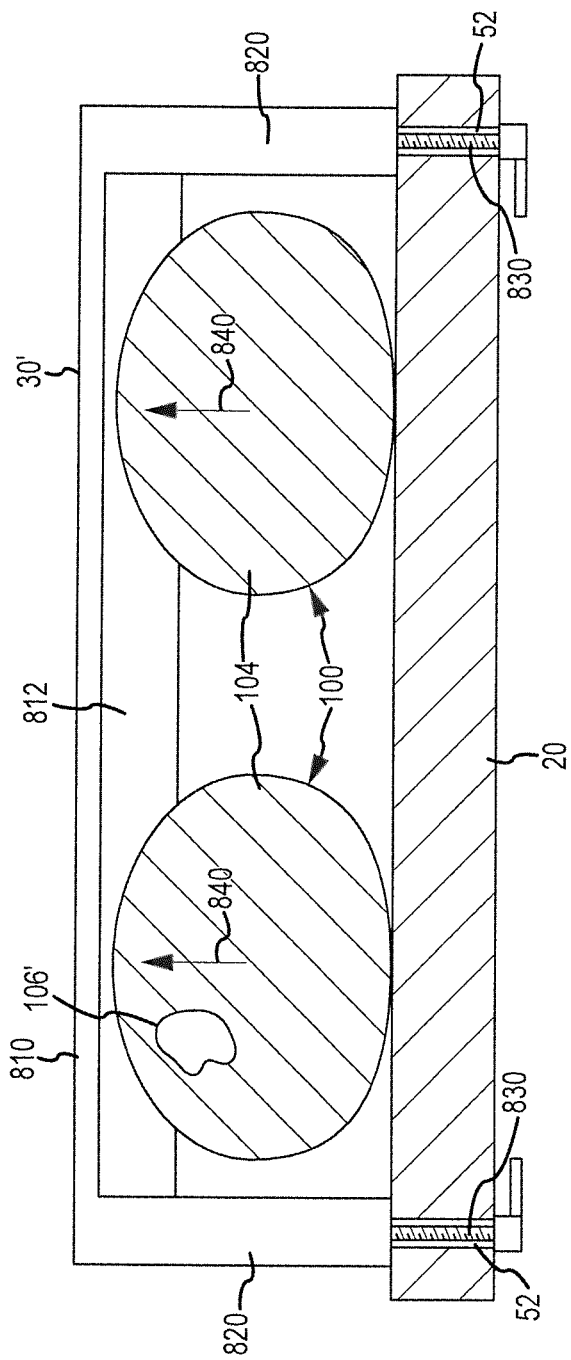
FIG. 8 is a cross sectional view taken along section line C-C in FIG. 7.

With further reference to FIGS. 7 and 8, an alternative embodiment of a first anchor 30' is shown. The first anchor 30' may be secured to the support member 20 and may extend over a portion of the leg 104 of the patient 100. In this regard, as can best be seen in FIG. 8, the patient's legs 104 may be generally disposed between the support member 20 and the first anchor 30. In this regard, the patient may exert a force against the first anchor 30' in the direction of arrows 840 in FIG. 8 corresponding to movement of the femur with respect to the lumbo-pelvic complex (i.e., to pull the knee away from the support member 20). This may result in flexing of one or more of the iliopsoas, anterior compartment of the thigh, gluteal muscles, and/or medial compartment of the thigh. Accordingly, the positioning of the patient 100 may be adjusted to image these muscles during the exertion by placement of the upper thigh area of the patient 100 in the imaging field 230 to identify a region of interest 106'. Thus, the portion 102' of the patient 100 imaged may correspond to a region containing the iliopsoas, anterior compartment of the thigh, gluteal muscles, and/or medial compartment of the thigh in the embodiment depicted in FIGS. 7 and 8.

The first anchor 30' may include one or more posts 820 extending from the support member 20 to a cross member 810. A cushioning member 812 may be disposed between the cross member 810 and the leg 104 of the patient 100 to prevent injury to the leg 104 of the patient 100 as the patient 100 exerts force against the cross member 810 in the direction of arrows 840. The posts 820 may receive fasteners 830 that may, for example, extend through the slot 52 provided in the support member 20. Alternatively, a separate through hole or series of through holes may be provided in the support member 20 through which the fastener 830 may be passed to secure the first anchor 30' relative to the support member 20.

Figure 9:
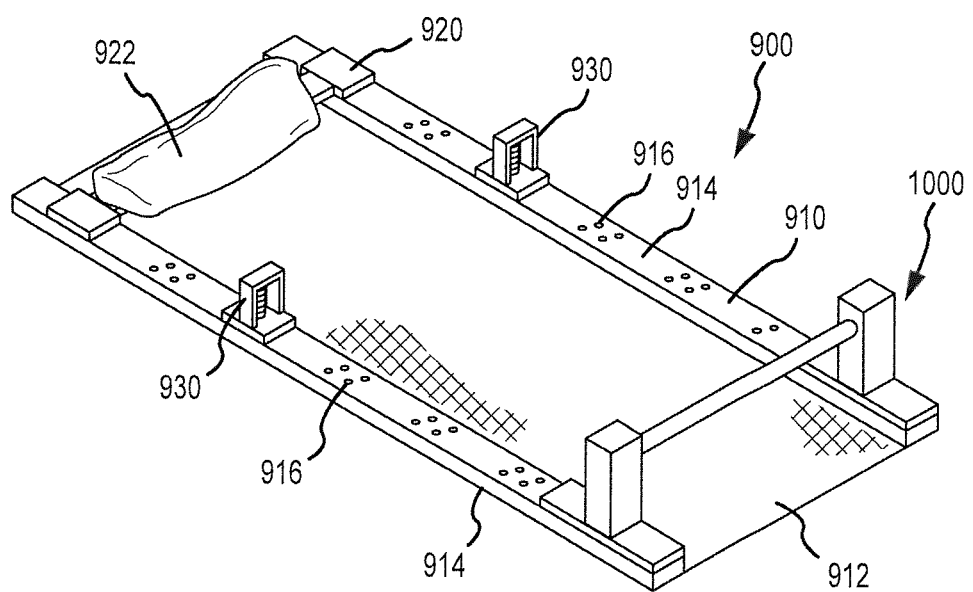
FIG. 9 is a perspective view of another embodiment of an apparatus.

With reference to FIG. 9, another embodiment of an apparatus 900 is depicted. The apparatus 900 may include a support member 910 and a first anchor (e.g., first anchor 1000 shown in FIG. 9 or alternative embodiments of first anchor 1100 or 1200 as shown in FIGS. 14-17). The apparatus 900 may also include second anchors 930. In this regard, a patient 100 may be supported by the apparatus 900 in a manner as described above, wherein the patient 100 may exert a force that is opposed by the first anchor 1000 and/or second anchor 930 such that the patient 100 may remain substantially stationary (e.g., so that an image may be obtained of the muscles used to exert the force that is opposed).

Figure 10:
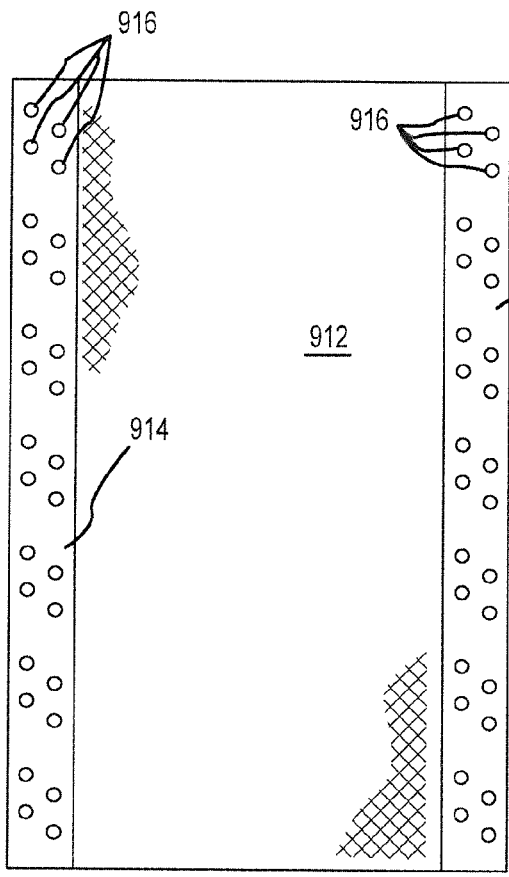
FIG. 10 is a top view of a support member according to the embodiment shown in FIG. 9.

With reference to FIG. 10, the support member 910 may include substantially rigid edge members 914. The edge member 914 may be disposed on opposite sides of the support member 910 and may extend longitudinally with respect to the support member 910. A pad 912 may extend between the edge members 914. The pad 912 may be constructed from a flexible material (e.g., a mesh material, a webbing material, a fabric, or other flexible material). In this regard, the pad 912 may facilitate folding the support member 910 (e.g., for storage when not in use). For instance, the pad 912 may allow the support member 910 to be folded or rolled up along a longitudinal axis of the support member 910. However, when the support member 910 is disposed in the unfolded position as shown in FIG. 9, the rigid edge members 914 may be sufficiently rigid to withstand substantial flexing (e.g., remain substantially stationary so as to allow for a clear imaging to be captured by an imaging device) in response to a patient 100 exerting a force on first anchor 1000 and/or second anchor 930.

The substantially rigid edge members 914 may also include a plurality of mounting holes 916. As will be appreciated with further reference to FIGS. 11A-16, the mounting holes 916 may coordinate with pegs 932 disposed on various members that may be attachably engaged with the rigid edge members 914. In this regard, various members may be attachably engaged with the rigid edge members 914 upon interaction of pegs 932 and mounting holes 916. Accordingly, a modular system may be provided where various members may be selectively attached depending upon the application in which the apparatus 900 may be used.

Figure 11A:
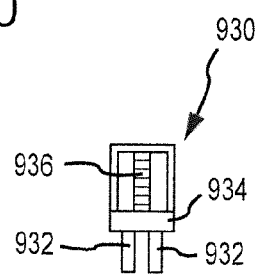
FIGS. 11A and 11B are side and top views, respectively, of an embodiment of a second anchor for use with the embodiment of FIG. 9.
Figure 11B:
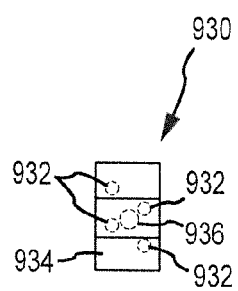
Figure 12:
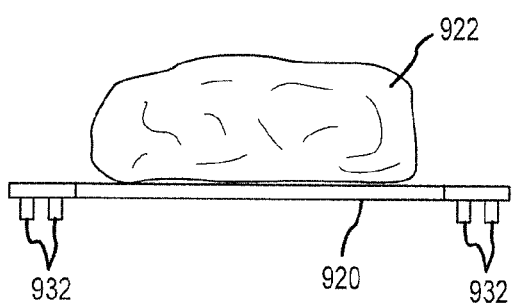
FIG. 12 is a side view of an embodiment of a stabilizing member for use with the embodiment of FIG. 9.

For example, the second anchors 930 shown in FIGS. 11A and 11B may include a plurality of pegs 932. The pegs 932 may be provided on the second anchor members 930 in a manner corresponding to the arrangement of the mounting holes 916 on the edge members 914 such that the pegs 932 may be received by corresponding ones of the mounting holes 916. In this regard, the second anchors 930 may be adjustably positioned with respect to the edge members 916 (e.g., based on a size of the patient 100).

The pegs 932 may extend from a base portion 934 of the second anchor 930. A handle 936 may extend from the base portion 934 that is graspable by a user 100 in a manner as described above with respect to second anchor 50.

Figure 13B:
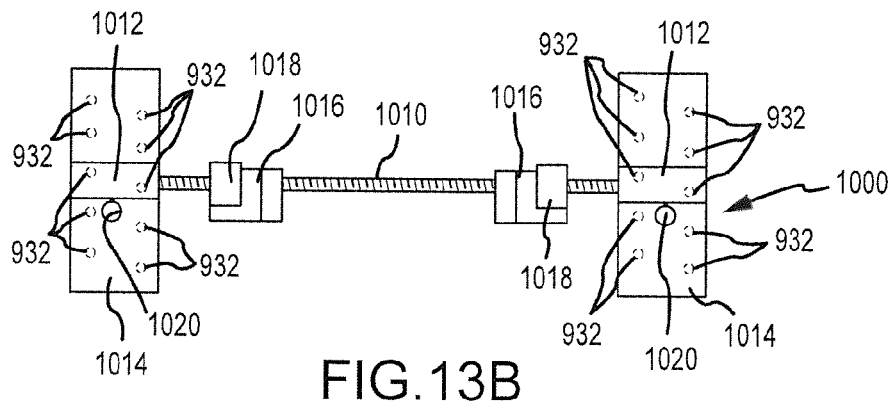
FIGS. 13A-13C various views, of an embodiment of a first anchor for use with the embodiment of FIG. 9.
Figure 13A:
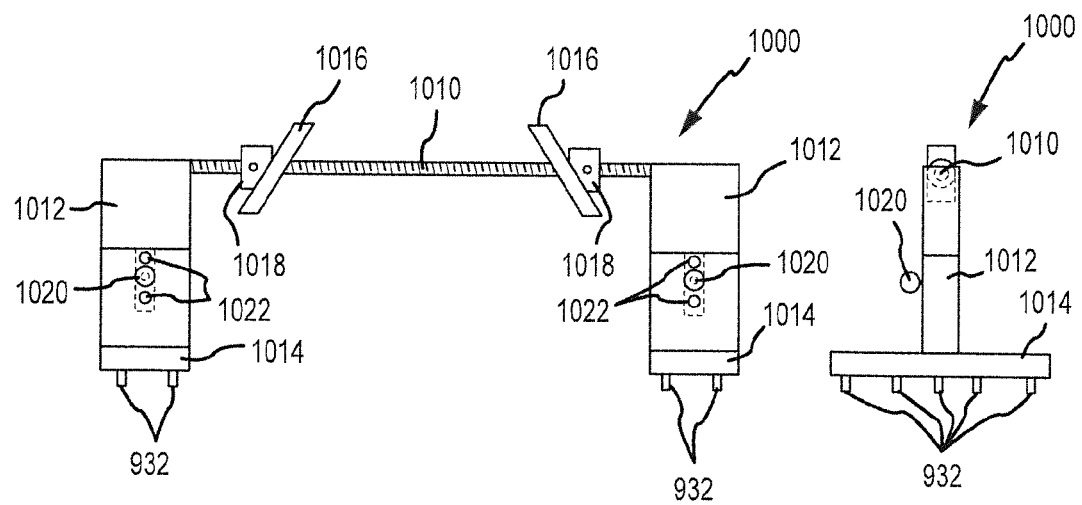
Figure 13C:
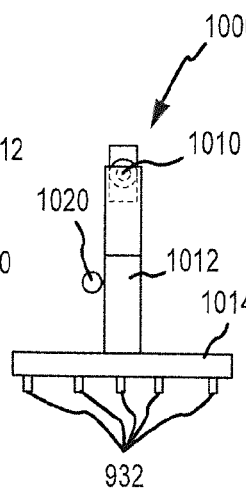

Additionally, an embodiment of a first anchor 1000 engageable with support member 910 is shown in FIGS. 13A-13B. The first anchor 1000 may include a plurality of pegs 932 that may coordinate with the mounting holes 916 of the support member 910 to secure the first anchor 1000 thereto. Furthermore, a rigid cross member 1010 may be provided between upright members 1012. The upright members 1012 may extend some distance away from a base portion 1014 engaged by way of the pegs 932 to the support member 910. In this regard, the rigid cross member 1010 may be spaced apart from the support member 910. Accordingly, the rigid cross member 1010 may be contacted by the foot 110 of the patient 100 (e.g., the ball of the patient's foot). The patient 100 may thus be able to apply a force to the rigid cross member 1010 that is opposed by the first anchor 1000.

One or more alignment guides 1016 may be provided that are attached to the rigid cross member 1010 by way of a clamplingly engageable collar 1018 that extends about the rigid cross member 1010. In this regard, the collars 1018 may be selectively adjustable along the length of the rigid cross member 1010 (e.g., to accommodate patients of different sizes). The alignment guides 1016 may contact the foot 110 of the patient 100 so as to dispose the foot 110 of the patient 100 in a desired position relative to the rigid cross member 1010 (e.g., in the lateral/medial direction). In this regard, particular muscles may be targeted to exert the force on the rigid cross member 1010 based on the orientation of the foot 110 of the patient 100 when applying the force. The upright members 1012 may be adjustable so as to dispose the rigid cross member 1010 nearer or farther from the support member 110. For example, the upright members 1012 may telescope to adjust the height of the upright members. Accordingly, the upright members 1012 may include a pin 1020 selectively engageable with a plurality of adjustment holes 1022 to maintain the upright members 1012 of different heights.

The first anchor 1000 may, when attached to the edge member 914 of the support member 910, maintain the edge members 914 at a distance corresponding to the width of the first anchor 1000 (e.g., the dimension corresponding to the fixed distance between base portions 1014). That is, because that pad 912 may be flexible, the edge members 914 may, absent some rigid link extending therebetween, move closer relative to one another. The first anchor 1000 may serve as a rigid link that maintains the edge member 914 a predetermined distance apart.

Additionally, a stabilizing member 920 may also be attached to the support member 910 by way of coordinating pegs 932 provided on the stabilizing member 920 and the mounting holes 916 provided on the edge members 914. For example, the stabilizing member may be attached to the support member 910 on a side of the support member 910 opposite the first anchor 1000. The stabilizing member 920 may act as another rigid link between the edge member 914. In this regard, despite a flexible pad 912 connecting the edge members 914, upon attachment of the first anchor 1000 and/or stabilizing member 920, the edge members 914 and stabilizing member 920 and/or first anchor 1000 may establish a substantially rigid frame. In that the stabilizing member 920 may be attached to the support member 910 on an end opposite the first anchor 1000, in some embodiments the stabilizing member 920 may be positioned adjacent to the head of the patient 100. In this regard, padding may be provided with the stabilizing member 920 such that the stabilizing member 920 may also include a pillow 922 for the patient when supported by the support member 910.

Figure 14:
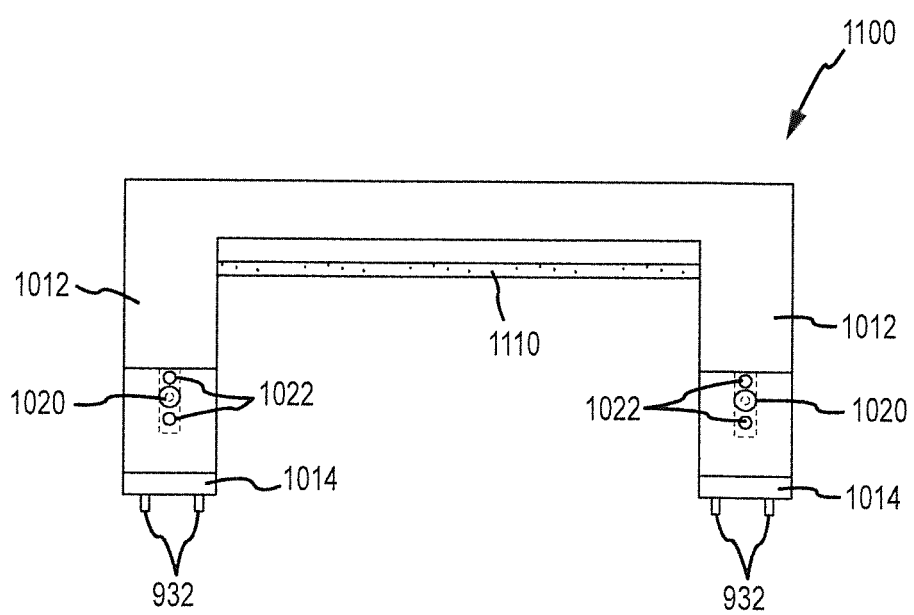
FIG. 14 is another embodiment of a first anchor for use with the embodiment of FIG. 9.

FIG. 14 depicts an alternative embodiment of a first anchor 1100 that may be secured to the support member 910 to oppose a force exerted by a patient 100 supported by the support member 910. The first anchor 1100 may include a resilient member 1110 extending between the upright members 1012. As such, the patient 100 may exert a force on the resilient member 1110. In this regard, rather than applying a force against the rigid cross member 1010, the patient 100 may apply a force that is opposed by the resilient member 1110. The resilient member 1110 may be adjusted or replaced to provide various levels of resistance to the application of force thereto by the patient.

Figure 16:
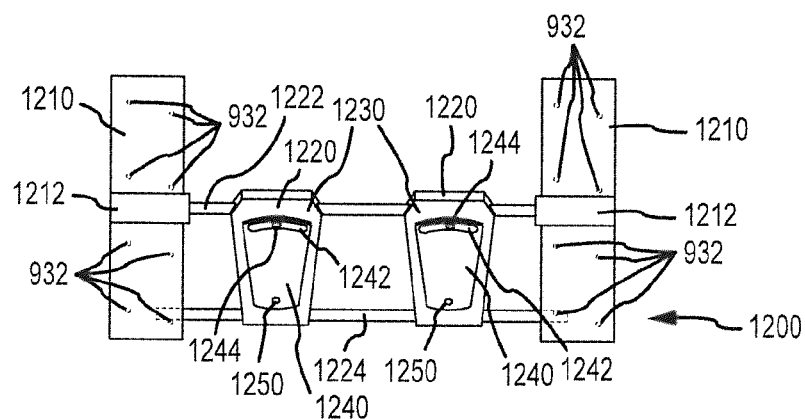
FIGS. 15-17 are various views of yet another embodiment of a first anchor for use with the embodiment of FIG. 9.
Figures 15, 17:
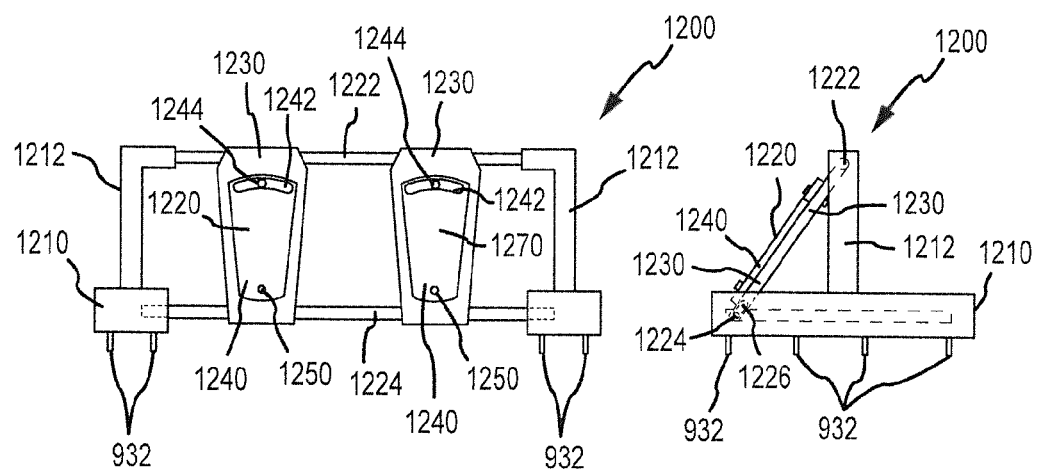

Still another embodiment of a first anchor 1200 is depicted in FIGS. 15-17. The first anchor 1200 may include base members 1210 that include pegs 932 to attach the base members 1210 to edge portions 914 by way of mounting holes 916 as described above. Upright members 1212 may extend from the base members 1210 and may be adjustable as described above with respect to first anchor embodiments 1000 and 1100. The first anchor 1200 may also include one or more foot pads 1220 that are contactable by the foot 110 (e.g., the plantar aspect of the foot 110 of the patient 100). The foot pads 1220 may be adjustable with respect to a direction corresponding to the dorsum and plantar directions as well as the medial and lateral directions of the foot 110 of the patient 100.

The foot pads 1220 may include a mounting member 1230 and a pivoting member 1240. In this regard, the mounting member 1230 may extend between a top cross member 1222 and a base cross member 1224. The top cross member 1222 may extend between the upright members 1212 adjacent to an end of the upright members 1230 opposite the base members 1210. The upright members 1212 may be adjustable in height so as to change the distance the top cross member 1222 is spaced from the base members 1210. The base cross member 1224 may extend between the base members 1210. The base cross member 1224 may be adjustably positionable along the base members 1210.

As can best be appreciated in FIG. 17, the mounting member 1230 of the foot pads 1220 may includes a slot 1226 that is engaged with the base cross member 1224. In this regard, upon adjustment of the height of the top cross member 1222 by adjustment of the upright members 1230 and/or positioning of the base cross member 1224 with respect to the base member 1210, the relative position of the foot pads 1220 in the dorsum/plantar directions relative to the foot 110 may be established. In this regard, relative positions corresponding to a range from acute angles between the dorsal aspect of the foot 110 and the tibia and obtuse angles between the dorsal aspect of the foot 110 and the tibia.

The pivot member 1240 of the foot pads 1220 may also be adjustable in the medial and lateral directions. In this regard, the pivot member 1240 may include a pivot 1250 at which the pivot member 1240 is pivotally mounted to the mounting member 1230. For example, the pivot member 1240 may pivot about the pivot 1250 in the medial and lateral direction. The pivot member 1240 may also include a slot 1242 in sliding engagement with a projection 1244 extending from the mounting member 1230. In this regard, the interaction of the slot 1242 and the projection 1244 may define an extent of adjustment of the pivot member 1240 of the foot pad 1220 in the medial and lateral directions.

Figure 18:
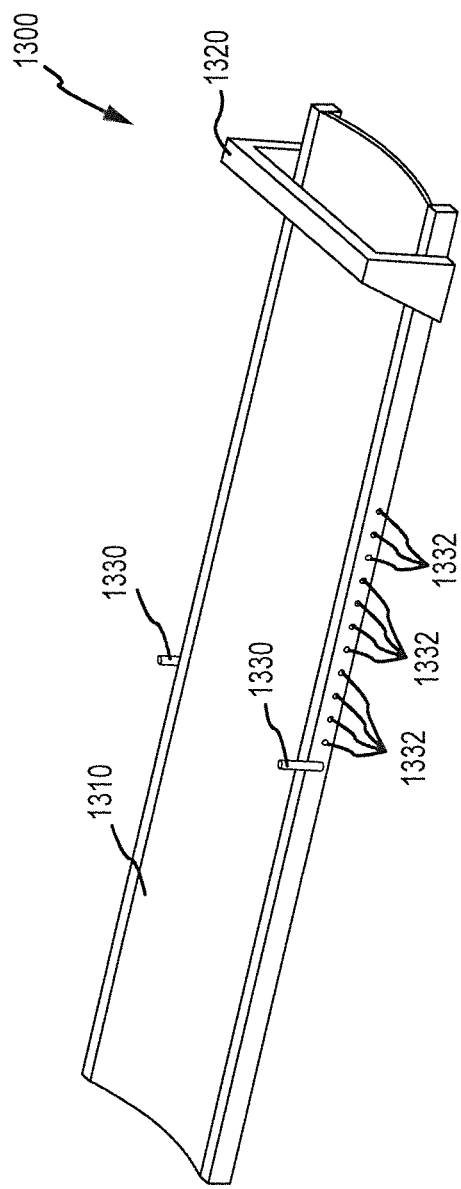
FIG. 18 is a perspective view of yet another embodiment of an apparatus.

FIG. 18 depicts yet another embodiment of an apparatus 1300. The apparatus 1300 may include first anchor 1320 extending from a support member 1310. As shown, the support member 1310. The support member 1310 may include a plurality of mounting holes 1332 to which second anchors 1330 may be affixed. In this regard, the second anchors 1330 may be adjustably positioned relative to the first anchor 1320.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Moreover, while the invention has primarily been described in the context of imaging a patient during exertion in connection with the identification, diagnosis, and/or treatment of exertional compartment syndrome, various aspects of the invention are applicable in other contexts. For example, the invention can be adapted to identify any condition that is apparent in imaging when the patient is exerting the muscle(s) being imaged. For example, the present invention may also be used in conjunction with identification, diagnosis, and/or treatment of popliteal artery entrapment syndrome. Accordingly, it should be understood that only some embodiment and variants thereof have been shown and described and that all changes and modifications that come within the spirit of the invention are desired to be protected.

What is claimed is:

1. A method for use of an apparatus for obtaining an image of a patient for determining a region of interest comprising venous compression adjacent to a compressing muscle flexed by the patient at a location in the patient downstream of an affected muscle relative to venous return flow in the vein compressed by the compressing muscle, the method comprising:
supporting a patient with respect to an imaging device on a patient support member, wherein at least a portion of the patient including the region of interest comprising venous compression adjacent to the compressing muscle flexed by the patient at the location in the patient downstream of the affected muscle relative to venous return flow in the vein compressed by the compressing muscle and a plurality of fiducial markings disposed on the patient support member relative to the portion of the patient are positionable in an imaging field of the imaging device; and
obtaining the image of the portion of the patient including the region of interest comprising venous compression adjacent to the compressing muscle flexed by the patient at the location in the patient downstream of the affected muscle relative to venous return flow in the vein compressed by the compressing muscle while the patient exerts a force by flexing the compressing muscle within the portion of the patient, wherein the force is opposed by a first anchor and the anchor is maintained in a fixed position relative to the patient support member during exertion of the force by the patient, and wherein the plurality of fiducial markings are apparent in the image and provide a reference in the image between the fiducial markings and the region of interest comprising venous compression adjacent to the compressing muscle flexed by the patient at the location in the patient downstream of the affected muscle relative to venous return flow in the vein compressed by the compressing muscle;
determining the location of the region of interest comprising venous compression adjacent to the compressing muscle flexed by the patient at the location in the patient downstream of the affected muscle relative to venous return flow in the vein compressed by the compressing muscle in the portion of the patient relative to the fiducial markings based on the image.

2. A method according to claim 1, wherein the region of interest is evident in the imaging field only during the exertion of the force using the muscle within the portion of the patient.

3. A method according to claim 2, further comprising:
diagnosing the patient based on the image.

4. A method according to claim 3, further comprising:
treating the patient at the region of interest.

5. A method according to claim 1, further comprising:
adjusting a second anchor relative to the first anchor, wherein the patient contacts the second anchor during the exertion of the force and the second anchor opposes the force and resists movement of the patient during the application of force.

6. A method according to claim 3, wherein the diagnosing comprises confirming the venous compression adjacent to the compressing muscle flexed by the patient at the location in the patient downstream of the affected muscle relative to venous return flow in the vein compressed by the compressing muscle.

7. A method according to claim 6, wherein the diagnosing comprises identifying the compressing muscle.

8. A method according to claim 4, wherein the treating comprises introducing an effective amount of a nerve-blocking toxin into the compressing muscle.

9. A method for use of an apparatus for obtaining an image of a patient for determining a region of interest comprising venous compression adjacent to a compressing muscle flexed by the patient at a location in the patient downstream of an affected muscle relative to venous return flow in the vein compressed by the compressing muscle, the method comprising:

supporting a patient with respect to an imaging device on a patient support member, wherein at least a portion of the patient including the region of interest comprising venous compression adjacent to the compressing muscle flexed by the patient at the location in the patient downstream of the affected muscle relative to venous return flow in the vein compressed by the compressing muscle is positionable in an imaging field of the imaging device; and obtaining the image of the portion of the patient including the region of interest comprising venous compression adjacent to the compressing muscle flexed by the patient at the location in the patient downstream of the affected muscle relative to venous return flow in the vein compressed by the compressing muscle while the patient exerts a force by flexing the compressing muscle within the portion of the patient, wherein the force is opposed by a first anchor and the anchor is maintained in a fixed position relative to the patient support member during exertion of the force by the patient; and determining the location of the region of interest comprising venous compression adjacent to the compressing muscle flexed by the patient at the location in the patient downstream of the affected muscle relative to venous return flow in the vein compressed by the compressing muscle in the portion of the patient based on the image.

10. A method according to claim 9, wherein the affected muscle is located in a limb of the patient.

11. A method according to claim 10, wherein the limb is the leg.

12. A method according to claim 11, wherein the compressing muscle is at least one of an adductor longus muscle, a sartorius muscle, a vastus intermedius muscle, an adductor magnus muscle, a popliteus muscle, a gastrocnemius muscle, a soleus muscle, and a plantaris muscle.

13. A method according to claim 9, further comprising:
treating the patient at the region of interest by introducing an effective amount of a nerve-blocking toxin into the compressing muscle.

14. A method according to claim 13, wherein the nerve-blocking toxin is human botulinum toxin.

15. A method according to claim 14, wherein the human botulinum toxin is onabotulinumtoxin A.

16. A method according to claim 15, wherein the human botulinum toxin is in solution form and diluted.

17. A method according to claim 13, wherein the effective amount is about 50 units to about 600 units per treatment.

18. A method according to claim 13, wherein the effective amount is about 50 to about 300 units per treatment.

19. A method according to claim 13, wherein the effective amount is about 50 to about 150 units per muscle per treatment.

20. A method according to claim 13, wherein the treating comprises introducing the nerve-blocking toxin into the compressing muscle percutaneously through at least one injection.

21. A method according to claim 9, further comprising:
determining a force value applied to the first anchor during flexing of the compressing muscle.

22. A method according to claim 21, further comprising:
monitoring the force value.

* * * * *

UNITED STATES PATENT AND TRADEMARK OFFICE
CERTIFICATE OF CORRECTION

PATENT NO. : 9,138,194 B1  
APPLICATION NO. : 13/871878  
DATED : September 22, 2015  
INVENTOR(S) : Joseph McGinley Page 1 of 1

It is certified that error appears in the above-identified patent and that said Letters Patent is hereby corrected as shown below:

IN THE CLAIMS

Column 15, Line 16, delete "includes" and insert therefor --include--

Signed and Sealed this  
First Day of March, 2016

Michelle K. Lee  
*Director of the United States Patent and Trademark Office*